(12) United States Patent
Schofield et al.

(10) Patent No.: US 6,479,714 B1
(45) Date of Patent: Nov. 12, 2002

(54) PROCESS FOR THE PREPARATION OF BUTANE TRIOLS

(75) Inventors: David Schofield, Middleton (GB); Mark Bailey, West Lothian (GB); Michael John Monteith, Rochdale (GB)

(73) Assignee: Avecia Limited, Manchester (GB)

( * ) Notice: Subject to any disclaimer, the term of this patent is extended or adjusted under 35 U.S.C. 154(b) by 367 days.

(21) Appl. No.: 09/242,899

(22) PCT Filed: Aug. 14, 1997

(86) PCT No.: PCT/GB97/02183

§ 371 (c)(1), (2), (4) Date: Feb. 26, 1999

(87) PCT Pub. No.: WO98/08793

PCT Pub. Date: Mar. 5, 1998

(30) Foreign Application Priority Data

Aug. 30, 1996 (GB) .............................................. 9618099

(51) Int. Cl.$^7$ .............................................. C07C 27/00
(52) U.S. Cl. ...................................................... 568/864
(58) Field of Search ......................................... 568/864

(56) References Cited

U.S. PATENT DOCUMENTS 2,683,721 A * 7/1954 Schlesinger ................. 568/864
4,410,744 A * 10/1983 Campbell .................... 568/864
4,973,769 A * 11/1990 Mueller ........................ 568/864
5,808,107 A 9/1998 Hollingsworth

FOREIGN PATENT DOCUMENTS

JP 6-172256 * 6/1994

OTHER PUBLICATIONS

Hajós, "Complex Hydrides and Related Reducing Agents in Organic Synthesis," pp. 46–58, 1979.*

Barnett, J. Chem. Soc., pp. 2743–2747, 1963.*

Pawlak, J. Org. Chem., vol. 52, pp. 2896–2901, 1987.*

* cited by examiner

Primary Examiner—Michael L. Shippen
(74) Attorney, Agent, or Firm—Rothwell, Figg, Ernst & Manbeck

(57) ABSTRACT

A process for the preparation of butane triols is provided. In the process, a malic acid diester is reduced with sodium borohydride in the presence of an ether and an alcohol. Preferably, the malic acid diester is an ethyl or methyl ester, the ether is tetrahydrofuran or bis(2-methoxyethyl) ether (diglyme), and the alcohol comprises ethanol. Advantageously, the reaction is carried out at ambient temperature.

19 Claims, No Drawings

PROCESS FOR THE PREPARATION OF BUTANE TRIOLS

This invention relates to a process for making butane triols and to butane triols made by the process.

Butane triols are valuable chemical intermediates for the pharmaceutical and agrochemical industries. For example butane triols are used in the preparation of antiviral compounds (U.S. Pat. No. 5,036,071) and platelet activating factors (Tet. Lett, vol 26, No. 42, pp 5195–5198, 1985). There is a need for commercially viable processes for the manufacture of butane triols which give a high yield of good quality product, are practical on large scale plant and do not produce foul odours.

A paper in Chemistry Letters, 1984, pp 1389–1392, published by The Chemical Society of Japan, described an attempted reduction of (S)-(−)-malic acid dimethyl ester in tetrahydrofuran using sodium borohydride but the resultant product consisted of multiple components which refused to be separated for structural diagnosis. Attempts using the pyrophoric and foul smelling borane-dimethyl sulphide complex gave the corresponding mono-ester in 88% yield and none of the triol was detected.

Reduction of malic acid dimethyl ester (also known as dimethyl malate) in ethanol using $KBH_4$ is described in J. Chem. Soc, 1963, pp 2743–7. However, this process gave only a 25% yield of butane-1,2,4-triol.

The Journal of Organic Chemistry, 1987, 52, pp 2896–2901 described the reduction of malic acid dimethyl ester on a small scale (600 mg) in $THF/H_2O$ (1:1, 15 ml) using an excess of sodium borohydride. Although this paper claims a 96% yield of (S)-(−)-butane-1,2,4-triol the present inventors were unable to achieve anywhere near this yield when they repeated the experiment several times. Furthermore the complex product was difficult to purify. There is also a risk of sudden and vigorous hydrogen release if the THF and water are immiscible and the sodium borohydride suddenly comes into contact with the water.

A paper in Heterocycles, vol 24, No. 5,1986, pp 1331–1346, describes the reduction of L-malic acid using diborane prepared in situ from the prior reaction of $BF_3$ etherate with sodium borohydride. However $BF_3$ etherate is expensive and unpleasant to handle because of its lachrymatory properties and diborane presents a potential fire hazard.

According to the present invention there is provided a process for preparing a butane triol comprising reduction of a malic acid diester in a mixture comprising an ether, an alcohol and sodium borohydride.

The malic acid diester can be an (R)-malic acid diester, (S)-malic acid diester or (R,S)-malic acid diester. The ester groups can be optionally substituted alkyl or aryl, for example optionally substituted phenyl esters, but are preferably alkyl esters. Especially preferred malic acid diesters are (R)-, (S)- and (R,S) malic acid diesters of the formula

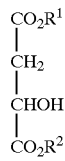

wherein $R^1$ and $R^2$ are each independently optionally substituted alkyl.

Preferably $R^1$ and $R^2$ are each independently $C_{1-4}$-alkyl, more preferably methyl or ethyl, especially methyl.

As examples of malic acid diesters there may be mentioned (R,S)-malic acid dimethyl ester, (R,S)-malic acid diethyl ester, (R,S)-malic acid methyl ethyl ester, (R,S)-malic acid diisopropyl ester and the corresponding (R)-malic acid diesters and (S)-malic acid diesters.

When the ester group is substituted, the substituent is preferably selected from the group consisting of alkoxy, such as C1-4 alkoxy; aryloxy, such as phenoxy; cyano and halo, such as bromo, but particularly fluoro or chloro, groups. Preferably, the ester group is unsubstituted.

The ratio of the ether to alcohol is preferably in the range 1:1 to 10:1, more preferably 1.5:1 to 9:1, especially 2:1 to 8:1 by weight.

Preferably the ratio of malic acid diester to mixture is preferably in the range of 1% to 25%, more preferably 10% to 23%, especially 12% to 20%, weight to volume (i.e. grams of malic acid diester per 100 ml in total of the alcohol and the ether used in the reduction process).

The number of moles of sodium borohydride used in the process preferably exceeds the number of moles of malic acid diester. Preferably there is used from 1.2 to 5.0 moles of sodium borohydride per mole of malic acid diester, more preferably 1.3 to 4.0.

The ether preferably has a boiling point above 50° C., more preferably above 60° C. For convenience the ether preferably has a boiling point below 200° C., more preferably below 175° C., because the ether is then removable on a rotary evaporator. In many embodiments, it is preferred that the ether is an alkyl mono-, di- or tri-ether in which each alkyl moiety comprises up to 3 carbon atoms, or is a cycloaliphatic ether. Examples of preferred alkyl mono-, di- or tri-ethers include diethyl ether, 1,2-diethoxyethane, 1,2-dimethoxyethane, bis(2-methoxyethyl) ether (diglyme), 2,2-dimethoxypropane and diisopropyl ether. Examples of preferred cycloaliphatic ether include 1,4-dioxane and particularly tetrahydrofuran. Especially preferred ethers are tetrahydrofuran and bis(2-methoxyethyl) ether (diglyme).

The alcohol is preferably an alkanol, more preferably an alkanol having at least two carbon atoms, especially a $C_{2-6}$-alkanol. Examples of suitable alkanols include ethanol, propan-1-ol, propan-2-ol, n-butanol, sec-butanol, tert-butanol and mixtures thereof. During the course of the process it is possible for trans-esterification to occur whereby the alcohol replaces some of the alcohol residues in the ester groups.

We have also found that by using an alkanol having at least two carbon atoms (e.g. a $C_{2-6}$-alkanol) the amount of sodium borohydride required is lower than when the alcohol is methanol and the process proceeds at a more controlled rate. As a result the process advantageously produces less hydrogen gas, reduction of the ester groups to hydroxy groups proceeds more efficiently and the process is cheaper to perform.

Accordingly a further aspect of the invention provides a process for preparing a butane trio comprising reduction of a malic acid diester in a mixture comprising an ether, an alkanol having at least two carbon atoms and sodium borohydride.

In light of the finding that less sodium borohydride is required when the process uses an alkanol having at least two carbon atoms it is preferred that the further aspect of the invention is performed in the presence of 1.3 to 2.5 moles, more preferably 1.4 to 2.0 moles of sodium borohydride per mole of malic acid diester.

We have also found that it is not always necessary to heat the reaction under reflux when ethanol is used as the alcohol, although heating under reflux may be performed if desired.

Accordingly the alkanol having at least two carbon atoms is preferably ethanol.

In light of the above a preferred process according to the invention is where
  (i) the butane triol is (R)-butane-1,2,4-triol, (S)-butane-1,2,4-triol or (R,S)-butane-1,2,4-triol;
  (ii) the ether is tetrahydrofuran or bis(2-methoxyethyl) ether (diglyme);
  (iii) the alcohol is ethanol, propan-1-ol, propan-2-ol, n-butanol, sec-butanol, tert-butanol or a mixture thereof;
  (iv) the ratio of the ether to the alcohol is in the range 1:1 to 10:1, by weight;
  (v) the ratio of malic acid diester to the mixture is in the range 1% to 25% weight to volume; and
  (vi) the number of moles of sodium borohydride is 1.2 to 5.0 moles of sodium borohydride per mole of malic acid diester.

Preferably the processes comprise adding a solution of the malic acid diester in an alcohol to a solution or suspension of sodium borohydride in THF or bis(2-methoxyethyl) ether (diglyme). The addition of diester to borohydride is preferably achieved incrementally or continuously over an addition period of from a few minutes up to several hours, for example from 30 minutes to 10 hours.

The process is preferably performed at a temperature in the range $-10°$ C. to $70°$ C., more preferably $-10°$ C. to $65°$ C. When the alcohol is ethanol the process can advantageously performed at $-10°$ C. to $30°$ C. and when the alcohol is iso-propanol, t-butanol or sec-butanol the process can advantageously performed at $10°$ C. to $60°$ C., more preferably $15°$ C. to $55°$ C. However, it is most preferred that the reaction is carried out at ambient temperature, such as from 15 to $25°$ C.

In a preferred embodiment the present process comprises the steps:
  (i) dissolving a malic acid diester in an alcohol, preferably an alkanol having at least two carbon atoms;
  (ii) adding the product of step (i) to a mixture of sodium borohydride and the ether;
  (iii) optionally heating the product of step (ii); and
  (iv) optionally separating the resultant butane triol from the ether, the alcohol and the sodium borohydride.

If desired, one or more dopants, e.g. potassium, lithium and/or calcium halides, may be included in the mixture. Preferably, such dopants if employed are included in small, for example, catalytic, amounts. Preferred dopants are LiCl and KCl. The dopant preferably is present in an amount of 0 to 20%, more preferably 0 to 15%, especially up to 0 to 10% by weight relative to the weight of sodium borohydride. Such dopants can be used to speed up the process, although in some cases one may not wish the process to proceed faster and the dopant is therefore omitted.

The reaction time of the process of the present invention will depend on a number of factors, for example the reagent concentrations, the relative amounts of reagents and particularly the reaction temperature. Typical reaction times, in addition to the reagent addition times, range from 1 hour to 48 hours, with reaction times of 3 to 20 hours being common. When the reaction is carried out at ambient temperature, reaction times of from 5 to 18 hours are often employed.

The invention is further illustrated by the following examples in which all parts and percentages are by weight unless specified otherwise. THF means tetrahydrofuran.

EXAMPLE 1

A solution of (S)-dimethyl malate (27 g, 160 m Mol) in methanol (150 ml) was added dropwise over a period of 120 minutes, with stirring, to a suspension of sodium borohydride (21 g, 555 m Mol) in THF (600 ml) at $20°$ C. to $30°$ C. The mixture was stirred at $20°$ C. to $30°$ C. for 30 minutes, then heated under reflux ($65°$ C.) for 1 hour. A considerable amount of hydrogen was released during addition of the methanol and refluxing. The mixture was cooled to $25°$ C. then methanol (750 ml) was added. The pH was lowered to pH7 using concentrated $H_2SO_4$. The resultant inorganic precipitate was filtered off, washed with methanol (2×100 ml) and the combined filtrate and washings were dried in vacuo to give (S)-1,2,4-butanetriol (17.9 g).

EXAMPLE 2

A solution of (S)-dimethyl malate (7.7 g, 46 m Mol) in industrial methylated spirits, (essentially ethanol, 12 ml) was added dropwise over a period of 60 minutes, with stirring, to a suspension of sodium borohydride (3.2 g, 83 m Mol) in THF (42 ml) at $25°$ C. The mixture was stirred under reflux for 2.5 hours. The mixture was cooled to room temperature then the pH adjusted to 7 using conc. HCl (7 ml). The inorganics were filtered-off and the filter cake washed with THF (2×25 ml). The filtrates were combined then concentrated to dryness in vacuo. The residue was dissolved in methanol (120 ml) and again concentrated to dryness in vacuo to give (S)-1,2,4-butanetriol (4.9 g, 95% yield).

EXAMPLE 3

A solution of dimethyl malate (8.4 g, 50 m Mol) in industrial methylated spirits (8 ml) at $25°$ C. was added dropwise with stirring over a period of 9 hours to a suspension of sodium borohydride (3.46 g, 89 m Mol) in THF (40 ml) at $0°$ C. After addition was complete the stirring was continued at $0°$ C. for a further 14 hours and the mixture was then warmed to $20°$ C. over 4 hours and kept at this temperature for 1 hour. The mixture was then cooled to $6°$ C. and acetone (11.4 ml) added over ½ hour. The mixture was cooled to $5°$ C. and conc. HCl (8 ml) added to lower the pH to 7. The mixture was screened, the cake washed with THF (2×25 ml) and the combined filtrates concentrated by drying in vacuo. Methanol (120 ml) was added to the material and the process repeated to give a quantitative yield of high purity butane-1,2,4-triol. The procedure produced very little hydrogen gas.

EXAMPLE 4

A solution of dimethyl malate (30.8 g, 186 m Mol) in propan-2-ol (70 ml) at $25°$ C. was added dropwise with stirring over a period of 6 hours to a suspension of sodium borohydride (13 g, 336 m Mol) in THF (210) at $50°$ C. Heating was removed as the addition starts so that the majority of the addition was carried out at 20–25° C.

The batch was held at 20–25° C. for 24–48 hours then acetone (50 ml) was added over ½ hour at below $30°$ C. The mixture was aged for ½ hour below $30°$ C. then methanol (50 ml) was added over ½ hour maintaining the temperature below $30°$ C. Again the mixture was aged for ½ hour. HCl was added (21 ml) to bring the pH to 7 at which point the batch was filtered, the cake washed with THF (56 ml) and the combined filtrates concentrated to dryness in vacuo. The residue was treated with methanol (200 ml) and the material concentrated to dryness in vacuo to give butane-1,2,4-triol, 16.7 g, 85%. This procedure produced very little hydrogen gas.

EXAMPLE 5

A solution of (S)-dimethyl malate (30.8 g, 186 m Mol) in propan-2-ol (62 ml) at 25° C. was added dropwise with stirring over a period of 6 hours to a suspension of sodium borohydride (13 g, 336 m Mol) in THF (160 ml) at 50° C. The reaction mass was aged for 1 hour at 50° C. then cooled to 25° C. and aged for 48 hours. The mixture was worked up as described in Example 4 to give (S)-butane-1,2,4-triol (16.7 g, 85% yield).

EXAMPLE 6

The method of Example 5 was repeated except that in place of propan-2-ol there was used tert-butanol. Very little hydrogen gas was produced during the process and the (S)-butane-1,2,4-triol was obtained in 80% yield.

EXAMPLE 7

A solution of (S)-dimethyl malate (1 g, 6.2 m Mol) in industrial methylated spirits, (1 ml) was added dropwise over a period of 60 minutes, with stirring, to a suspension of sodium borohydride (0.42 g, 11.1 m Mol) in THF (5 ml) at 25° C. The mixture was stirred at 20 to 30° C. for 16 hours and then the pH adjusted to 7 using conc. HCI (1 ml). The inorganics were filtered-off and the filter cake washed with THF (2×3.5 ml). The filtrates were combined then concentrated to dryness in vacuo. The residue was dissolved in methanol (15 ml) and again concentrated to dryness in vacuo. The dissolution in methanol and concentration to dryness was repeated two further times to give (S)-1,2,4-butanetriol (0.59 g, 90% yield).

EXAMPLE 8

A solution of (R)-dimethyl malate (2.11 g, 13 m Mol) in industrial methylated spirits, (2 ml) was added dropwise over a period of 60 minutes, with stirring, to a suspension of sodium borohydride (0.91 g, 23.4 m Mol) in THF (10 ml) at 25° C. The mixture was stirred at 20 to 30° C. for 16 hours and then the pH adjusted to 7 using conc. HCI (1 ml). The inorganics were filtered-off and the filter cake washed with THF (2×6.5 ml). The filtrates were combined then concentrated to dryness in vacuo. The residue was dissolved in methanol (31 ml) and again concentrated to dryness in vacuo. The dissolution in methanol and concentration to dryness was repeated two further times to give (R)-1,2,4-butanetriol (0.59 g, 90% yield).

EXAMPLE 9

The method of Example 7 was repeated, except employing bis(2-methoxyethyl) ether (diglyme) in place of THF to give (S)-1,2,4-butanetriol (0.57 g, 87% yield).

COMPARATIVE EXAMPLE A—THF SOLVENT

To a solution of dimethyl malate (0.6 g, 3.7 m Mol) in THF (15 ml) was added sodium borohydride (0.2 g, 5 mmol) at 25° C. The mixture was stirred for 20 minutes during which time the viscosity increased to a level which made the further processing steps difficult. 30 ml of methanol was added and the pH was brought to 7 using Dowex 50WX8 Resin. The mixture was filtered then solvent stripped off in vacuo. Methanol (10 ml) was added and again the mixture concentrated to dryness by evaporation to give butane-1,2,4-triol in a yield of about 50% along with other components.

COMPARATIVE EXAMPLE—INDUSTRIAL METHYLATED SPIRITS SOLVENT

A solution of dimethyl malate (4.1 g, 25 m Mol) in industrial methylated spirits (10 ml) was added to a suspension of sodium borohydride (1.9 g, 50 m Mol) in industrial methylated spirits (35 ml) at 20° C. over 2 hours. The mixture was stirred for 16 hours at 20–30° C. then adjusted to pH7 with concentrated $H_2SO_4$. The mixture was filtered and the organic filtrate concentrated in vacuo. The filter cake was washed with methanol (75 ml) and the wash combined with the concentrated filtrate. This solution was then concentrated in vacuo to give butane-1,2,4-triol (2.8 g, 50–60% pure).

What is claimed is:

1. A process for preparing a butane triol comprising reduction of a malic acid diester in a mixture comprising an ether an alcohol and sodium borohydride.

2. A process according to claim 1 wherein the malic acid diester is an (R)-, (S)- or (R,S)- malic acid diester of the formula:

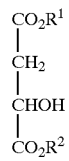

wherein $R^1$ and $R^2$ are each independently optionally substituted alkyl.

3. A process according to claim 2, wherein $R^1$ and $R^2$ are independently methyl or ethyl groups.

4. A process according to claim 1, wherein the weight ratio of ether to alcohol is 2:1 to 8:1.

5. A process according to claim 1, 2, 3 or 4, wherein the ether has a boiling point above 50° C. and below 200° C.

6. A process according to claim 5, wherein the ether is an alkyl mono-, di- or tri-ether in which each alkyl moiety comprises up to 3 carbon atoms, or is a cycloaliphatic ether.

7. A process according to claim 6 wherein the ether is tetrahydrofuran or bis(2-methoxyethyl) ether.

8. A process according to claim 1, 2, 3 or 4, wherein the alcohol is an alcohol having at least two carbon atoms.

9. A process according to claim 8, wherein the number of moles of the sodium borohydride is present in an amount of 1.3 to 2.5 moles per mole of malic acid diester.

10. A process according to claim 8, which is performed at a temperature in the range of about −10° C. to about 70° C.

11. A processing according to claim 10 which is performed at 10° C. to 60° C. and the alcohol is iso-propanol, t-butanol or sec-butanol.

12. A process according to claim 8, wherein the mixture contains from 0 to about 20% of a catalytic dopant by weight relative to the weight of sodium borohydride.

13. A processing according to claim 1, 2, 3 or 4, which is performed at a temperature in the range −10° C. to 70° C.

14. A process according to claim 1, 2, 3 or 4, wherein the mixture contains from 0 to 20% of a catalytic dopant by weight relative to the weight of sodium borohydride.

15. A process according to claim 1, 2, 3 or 4, wherein the ether is an alkyl mono-, di-, or tri-ether in which alkyl moiety comprises up to about 3 carbon atoms, or is a cycloaliphatic ether, the alcohol is an alcohol having at least two carbon atoms and the sodium borohydride is present in an amount of about 1.3 to about 2.5 moles per mole of malic acid diester.

16. A process according to claim 15 which is performed at a temperature in the range −10° C. to 30° C. and the alcohol is ethanol.

17. A process according to claim 15, wherein the mixture contains from 0 to about 20% of a catalytic dopant by weight relative to the weight of sodium borohydride.

18. A process for preparing a butane triol comprising reduction of a malic acid diester in a mixture comprising an ether, an alcohol and sodium borohydride comprising the steps:
  (i) dissolving the malic acid diester in the alcohol;
  (ii) adding the product of step (i) to a mixture of sodium borohydride and the ether;
  (iii) optionally heating the product of step (ii); and
  (iv) optionally separating the resultant butane triol from the ether, the alcohol and the sodium borohydride.

19. A process for preparing a butane triol comprising the reduction of a malic acid diester in a mixture comprising an ether, an alcohol and sodium borohydride wherein:
  (i) the butane triol is (R)-butane-1,2,4-triol, (S)-butane-1,2,4-triol or (R,S)-butane-1,2,4-triol;
  (ii) the ether is tetrahydrofuran or bis(2-methoxyethyl) ether;
  (iii) the alcohol is ethanol, propan-1-ol, propan-2-ol, n-butanol, sec-butanol, tert-butanol or a mixture thereof;
  (iv) the ratio of the ether to the alcohol is in the range of 2:1 to 8:1, by weight;
  (v) the ratio of malic acid diester to the mixture is in the range of 1% to 25% weight to volume; and
  (vi) the number of moles of sodium borohydride is 1.2 to 5.0 moles of sodium borohydride per mole of malic acid diester.

* * * * *